United States Patent
Millenbaugh et al.

(10) Patent No.: US 9,993,660 B2
(45) Date of Patent: Jun. 12, 2018

(54) METHOD OF USING LASER-INDUCED OPTOACOUSTICS FOR THE TREATMENT OF DRUG-RESISTANT MICROBIAL INFECTIONS

(71) Applicants: Nancy Millenbaugh, San Antonio, TX (US); Mauris DeSilva, Austin, TX (US); Jonathan Baskin, San Antonio, TX (US); William R. Elliot, San Antonio, TX (US)

(72) Inventors: Nancy Millenbaugh, San Antonio, TX (US); Mauris DeSilva, Austin, TX (US); Jonathan Baskin, San Antonio, TX (US); William R. Elliot, San Antonio, TX (US)

(73) Assignee: The United States of America as rep. by Secretary of the Navy, Washington, DC (US)

( * ) Notice: Subject to any disclaimer, the term of this patent is extended or adjusted under 35 U.S.C. 154(b) by 127 days.

(21) Appl. No.: 13/900,994

(22) Filed: May 23, 2013

(65) Prior Publication Data

US 2014/0350452 A1 Nov. 27, 2014

(51) Int. Cl.
| | | |
|---|---|---|
| *A61K 39/395* | (2006.01) | |
| *A61K 39/40* | (2006.01) | |
| *A61K 39/02* | (2006.01) | |
| *A61N 5/06* | (2006.01) | |
| *A61K 45/06* | (2006.01) | |
| *A61K 41/00* | (2006.01) | |
| *A61K 47/68* | (2017.01) | |
| *A61K 47/69* | (2017.01) | |
| *A61N 5/067* | (2006.01) | |

(52) U.S. Cl.
CPC .......... *A61N 5/062* (2013.01); *A61K 41/0052* (2013.01); *A61K 45/06* (2013.01); *A61K 47/6835* (2017.08); *A61K 47/6923* (2017.08); *A61N 5/0624* (2013.01); *A61N 2005/067* (2013.01)

(58) Field of Classification Search
CPC .................. A61K 9/14; A61K 41/0057; A61K 47/48561; A61K 45/06; A61K 9/00; A61K 9/16; A61K 9/51
USPC ......... 424/130.1, 163.1, 164.1, 178.1, 184.1, 424/234.1
See application file for complete search history.

(56) References Cited

U.S. PATENT DOCUMENTS 8,137,698 B2 * 3/2012 Peyman ........................ 424/489
2010/0278923 A1 * 11/2010 Chen .................... A61K 9/5115
424/490

OTHER PUBLICATIONS

Zharov, V.P., et al. Biophysical Journal, vol. 90, pp. 619-627, Jan. 2006.*
Biophys J. Jan. 15, 2006;90(2):619-27. Epub Oct. 20, 2005. Photothermal nanotherapeutics and nanodiagnostics for selective killing of bacteria targeted with gold nanoparticles. Zharov VP, Mercer KE, Galitovskaya EN, Smeltzer MS.
PLoS One. 2012;7(9):e45557. doi: 10.1371/journal.pone.0045557. Epub Sep. 26, 2012. In vivo magnetic enrichment, photoacoustic diagnosis, and photothermal purging of infected blood using multifunctional gold and magnetic nanoparticles. Galanzha EI, Shashkov E, Sarimollaoglu M, Beenken KE, Basnakian AG, Shirtliff ME, Kim JW, Smeltzer MS, Zharov VP.

* cited by examiner

*Primary Examiner* — Rodney P Swartz
(74) *Attorney, Agent, or Firm* — Albert Chunilla; Ning Yang; Diane Tso

(57) ABSTRACT

The present invention is related to novel functional antibody coated nanoparticles, and the preparation method thereof. The functional antibody coated nanoparticles according to the present invention can be used as photothermal agents to effectively inhibit the growth of microbes including drug-resistant strains and biofilm with laser irradiation.

6 Claims, 4 Drawing Sheets

Figure 1:
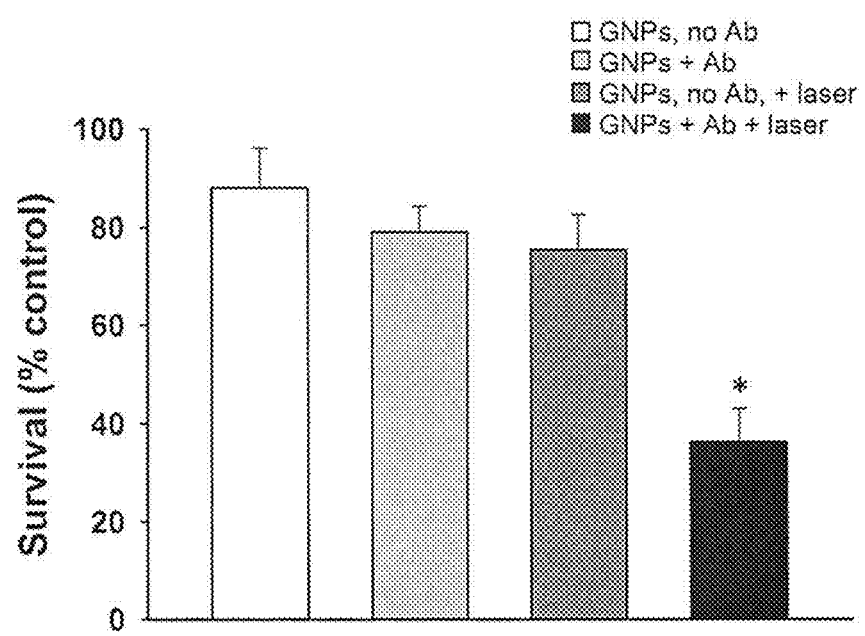

METHOD OF USING LASER-INDUCED OPTOACOUSTICS FOR THE TREATMENT OF DRUG-RESISTANT MICROBIAL INFECTIONS

BACKGROUND OF INVENTION

A major cause of serious battlefield injuries during Operations Iraqi Freedom and Enduring Freedom has been the use of improvised explosive devices against coalition troops. Maxillofacial, head, and neck regions are particularly at risk for injury and pose distinct treatment challenges to clinicians (1, 2). These combat associated traumatic wounds are different from injuries experienced in the civilian sector due to massive tissue damage from extremely high velocity, high-energy projectiles, involvement of blast wave effects, and a higher rate of wound contamination from the environment (2). Previous studies indicate a significant percentage of these wounds were infected with multi-drug resistant bacteria such as methicillin resistant *Staphylococcus aureus* (MRSA) (1). In addition to those injured in combat, military recruits are one of the groups identified as at risk for acquiring MRSA infections. This is notable because those affected are typically young, healthy individuals without any apparent risk factors, and these infections have been associated with an increased incidence of hospitalizations. Because emergence of multi-drug resistant bacterial infections is a growing problem in military and civilian populations worldwide, novel anti-microbial therapies are needed as alternatives to traditional antibiotic regimens.

Current treatment regimens for bacterial infections focus on use of antibiotics. The challenges associated with the successful treatment of microbial infections are increasing because the rate by which bacteria develop resistance to current treatment modalities outpaces the development of new antibiotics. *S. aureus* is the most common pathogen isolated from patients, and methicillin resistant strains now account for approximately 60% of *S. aureus* isolates in intensive care units in the US (3). Vancomycin is commonly used to treat serious MRSA infections because most strains of the pathogen exhibit resistance to many other classes of antimicrobials. However, cases of MRSA with reduced susceptibility or resistance to vancomycin have begun to emerge in hospitals and are associated with increasing patient mortality (4). The continued development of bacterial resistance indicates an urgent need for treatment approaches that do not rely solely upon antibiotics.

One approach being tested by several groups is photodynamic therapy, which uses light absorbing dyes to generate toxic oxygen radicals to kill the bacteria. However, this treatment might not be effective for infections in hypoxic wound environments (5). Another promising approach is to use metal nanoparticles, and laser energy to physically damage the bacteria.

The optical properties of conductive metal nanoparticles (NPs), such as those made of gold and silver have been associated with the surface plasmon resonance (SPR) of metals, which when confined to small colloids, is referred to as the localized surface plasmon resonance (LSPR). This phenomenon, in which the free electrons oscillate collectively on the metal surface when irradiated with particular energies of light, causes wavelength dependent absorption and scattering of light, and is the source of the colors associated with metal nanoparticles. The size, shape, and composition of the colloidal particles determines the energy of the SPRs, and therefore, control over the synthesis of metal NPs provides an ability to tune the optical properties of the nanometals contained therein.

Metal nanoparticles, due to their relative inertness, sub-100 nm size, unique electromagnetic properties, and strong optical tunability, have attracted attention in the biomedical field. For example, because SPRs enhance many optical processes, including Raman scattering, fluorescence, and two-photon excited luminescence, gold NPs have been used in optical diagnostics and as contrast agents for bioimaging. When gold NPs absorb light energy, they also release heat, making them useful in photothermal therapy applications targeting cancer and bacterial cells. Laser-induced photothermal phenomena induce physical disruption of the bacterial cells leading to death. This is a different type of killing mechanism than that caused by antibiotics or photodynamic therapies that induce chemical damage via generation of oxygen radicals. Resistance to photothermal destruction has not been reported in the literature.

Despite the prospect of biomedical utilizations of metal NPs, the use of metal NPs for medical diagnosis and treatment is limited, because NPs cannot be fully integrated into the biological realm without changes to their surface chemistry. Biomolecules interact with cells through a multitude of chemical interactions and physical forces. The interactions between biological systems and metal NPs, on the other hand, are non-specific. In order to realize the full biomedical potential of metal nanoparticles, the nanoparticles must interact specifically with biological matter, including cell surface components. At the same time, nanoparticle aggregation and nonspecific interactions with molecular and cellular constituents of the biological system must be minimized. Thus, there is a need in the art for metal nanoparticles that can be readily modified to precisely control their electromagnetic and biofunctional properties.

Zharov et al. taught a method using gold nanospheres and pulsed laser irradiation to induce a photothermal effect for bacterial destruction (5). This method involved a two-step process to bind the particles to the bacteria, where bacteria were first incubated with primary antibody against *S. aureus* Protein A in the cell wall then incubated with gold nanospheres coated with a secondary antibody against the primary antibody. However, the Zharov et al. (5, 7) only tested the technique against methicillin sensitive bacteria. The method's effectiveness against drug resistant bacteria is not addressed. Furthermore, the level of expression of Protein A, which is the targeted protein of Zharov study, has been reported to vary among different strains of MRSA and among the different phases of growth of the bacteria (6). As a result, the Zharov method is likely to be ineffective against strains or phases of the bacteria that fails to express Protein A.

DETAILED DESCRIPTION OF DRAWINGS

FIG. 1 Targeted killing of Methicillin sensitive (MSSA) with antibody functionalized gold nanoparticles (GNPs) combined with 532 nm laser irradiation (100 pulses, 5 J/cm2), *p=0.0002 compared to other three experimental groups determined by one-way ANOVA followed by post-hoc Tukey HSD test.

Figure 2:
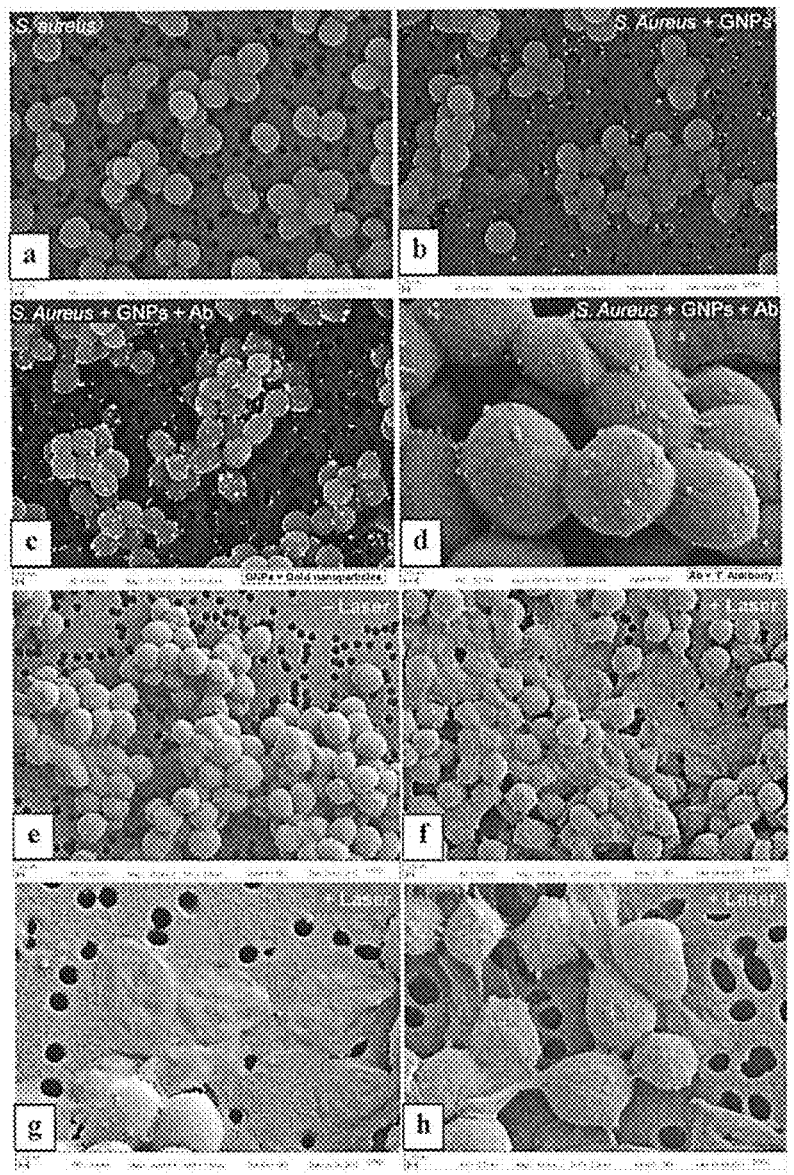

FIG. 2 Scanning electron microscope images of a) MSSA, b) MSSA+GNPs without antibody, c) MSSA+GNPs with antibody at 25,000×, d) MSSA+GNPs with antibody at 100,000× magnification, e) MSSA+GNPs with antibody and exposed to sham laser treatment (−Laser), and f) through h) MSSA+GNPs with antibody and exposed to pulsed laser irradiation at 532 nm (+Laser).

Figure 3:
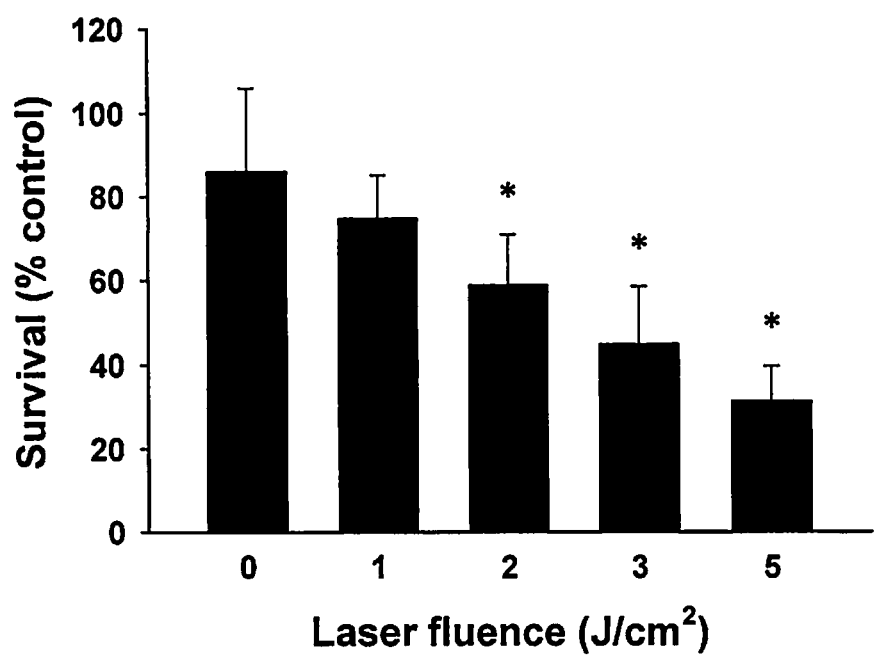

FIG. 3 Antibacterial effect of antibody targeted gold nanoparticles and pulsed 532 nm laser irradiation against MSSA as a function of laser fluence. *$p \leq 0.006$ based upon one-way ANOVA followed by post hoc Dunnett test using the 0 J/cm2 group as control for the comparison against the other experimental groups.

Figure 4:
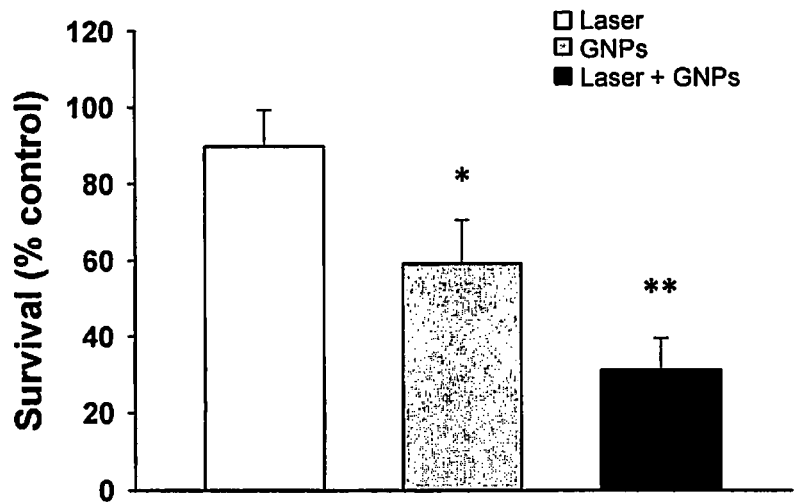
Figure 4:
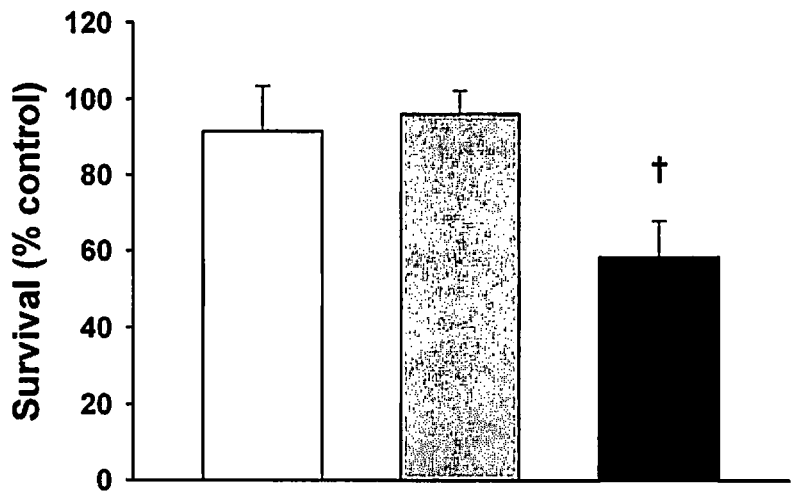

FIG. 4 Antibacterial effect of targeted GNPs and pulsed 532 nm laser irradiation against A) MSSA and B) MRSA, *$p=0.02$ compared to the "Laser" group. **$p=0.001$ compared to the "Laser" group and $p=0.03$ compared to the "GNPs" group, Panel B.) †$p=0.01$ compared to the "Laser" and "GNPs" groups.

DETAILED DESCRIPTION OF THE INVENTION

An objective of this invention is a non-antibiotic treatment method for microbial infections.

Another objective of this invention is functional antibody coated nanoparticles for selective killing of drug resistant bacteria. The inventive method simplifies the treatment protocol of Zharov et al. by requiring attachment of only one antibody, and is effective against both methicillin sensitive and resistant bacteria.

Yet another objective of this invention is a method of destroying/reducing microbial biofilm using functional antibody coated nanoparticles under exposure of laser irradiation.

Yet another objective of this invention is a method of destroying/reducing bacterial infection including infections involving biofilm generated by microorganisms using functional antibody coated nanoparticles, in combination with an adjuvant under laser irradiation.

An embodiment of this invention is functional antibody coated nanoparticles comprised of a nanoparticle core; and an antimicrobial antibody coating disposed on at least part of the surface of the nanoparticle core. The nanoparticle core is capable of absorbing laser irradiation, which includes but is not limited to a metal nanoparticle, a nanoparticle with a core-shell structure, or an electroceramic nanocomposite. In one embodiment, the nanoparticle core is a gold nanoparticle or a silica nanoparticle coated with a gold shell. The antimicrobial antibody is capable of recognizing the target microorganism such as a Gram-positive or Gram-negative bacterium. In one embodiment, the antibody is capable of recognizing bacteria with surface peptidoglycan. The antibody may be coated onto the nanoparticle core via a variety of attachment methods, including but not limited to covalent bonds, electrostatic interactions, or streptavidin-biotin bond.

The functional antibody coated nanoparticles of this invention may be easily prepared by a) providing a nanoparticle solution; preparing a solution containing the antibacterial antibody; and reacting said nanoparticle solution with the antibacterial antibody solution, so the antibacterial antibody is fixed on a surface of the nanoparticle. In one embodiment of this invention, gold nanoparticle is first coated with streptavidin. Streptavidin coated gold nanoparticles are purchased from BIOASSAY WORKS®, LLC (Ijamsville, Md.), and suspended in a phosphate buffered saline solution containing bovine serum albumin and glycerol to stabilize the nanoparticles against aggregation. An anti-peptidoglycan antibody solution is then prepared, which contains biotinylated antipeptidoglycan antibody. The two solutions are thoroughly mixed, and the antipeptidoglycan antibody is fixed onto the surface of the nanoparticle via streptavidin-biotin binding.

The functional antibody coated nanoparticle of this invention may be used to treat microbial infection, such as a bacteria infection. In an embodiment, the subject is first administrated an effective dose of the antibody coated nanoparticles of this invention, and the subject was placed under laser irradiation source. The exposure may last approximately 1-200 seconds. The laser irradiation source may include but not be limited to any high energy light source with pulse width less than 100 microseconds. The wavelength of the irradiation may be 300 to 1500 nm. In one embodiment, a patient was treated for wound surface bacterial infection by first applying functional antibody coated nanoparticles to the wound, and then irradiating the wound site under high peak power pulsed laser for a short time. A pharmaceutically acceptable carrier such as a liquid, solution, or aerosol composed of sterile, isotonic saline, phosphate buffered saline or 0.1% albumin in saline for topical administration, may also be administered with the functional antibody coated nanoparticles. One or more antimicrobial agents may also be administered before laser irradiation. For example, Chitosan is a naturally occurring biopolymer with good biocompatibility and antimicrobial activity against a wide range of bacteria. Endopeptidase lysostaphin can enzymatically attack the bacterial cell wall. Other antimicrobial enzymes, such as dispersin B that breaks down the extracellular matrix of biofilms, and antimicrobial peptides, such as LL-37 and ranalexin that weaken the bacterial membrane or cell wall, may also be included.

The functional antibody coated nanoparticles may also be used to prevent or reduce biofilm formation generated by a microorganism, such as bacteria. In an embodiment, the subject is administrated an effective dose of the functional antibody coated nanoparticles of this invention, and subject to laser irradiation. The exposure may last approximately 1-200 seconds. The laser irradiation source may include but not limited any high energy light source with a pulse width less than 100 microseconds. The wavelength of the irradiation may be 300 to 1500 nm. A pharmaceutically acceptable carrier such as a liquid, solution, or aerosol composed of sterile isotonic saline, phosphate buffered saline, 10% glycerol, or 0.1% albumin in saline for topical administration, may also be administered with the functional antibody coated nanoparticles. One or more antimicrobial agents may also be administered before laser irradiation. For example, Chitosan is a naturally occurring biopolymer with good biocompatibility and antimicrobial activity against a wide range of bacteria. Endopeptidase lysostaphin can enzymatically attack the bacterial cell wall. Dispersin B is also known to break down the extracellular matrix of staphylococcal biofilms (12). Antimicrobial peptides such as LL-37 and ranalexin weaken the bacterial membrane or cell wall (13, 14).

Although the embodiment is directed to *S. aureus*, other bacterial infections may also be treated using nanoparticles of this invention, such as *Acinetobacter baumanii, Pseudomonas aeruginosa, E. coli*, and *Klebsiella* species. Antibodies specific for the infectious agent must be selected to target the nanoparticles to the bacteria. Nanoparticles of different shapes or sizes must be selected based on the wavelength selected for the infection to maximize absorption.

Similarly, in additional to treating topical wounds, infection within the body such as lung infection caused by tuberculosis may also be treated using the inventive method with minor adaption. The laser wavelength for deeper penetration needs to be in the near infrared region of 700 to 900 nm. Laser irradiation may be directed to infection site via optic fibers.

Example 1

Preparation Of Functionalized Gold Nanoparticles

Fifty μL aliquots (~6.5×10$^{10}$ particles) of sterile-filtered 40 nm gold nanospheres coated with streptavidin (15 OD, BioAssay Works, Ijamsville, Md., USA) were diluted with 1 mL of phosphate buffered saline (PBS, Gibco, Grand Island, N.Y., USA) containing 0.1% bovine serum albumin (Sigma, St. Louis, Mo., USA) and 10% glycerol (Sigma, vehicle containing PBS, bovine serum albumin, and glycerol hereafter referred to as PBG) and centrifuged at 7400 g for 10 minutes at room temperature to remove the original vehicle.

The supernatant was removed, the pellet was suspended in 0.5 mL of PBG, and biotinylated anti-*Staphylococcus aureus* monoclonal antibody (1.3 mg/mL, Clone 702, Aeris Antibodies, San Diego, Calif., US) was added at a 1:100 volumetric ratio. Non-functionalized gold nanospheres were prepared in the same way without addition of the antibody. Tubes were then placed on an orbital mixer (Clay Adams Nutator Mixer, BD, Franklin Lakes, N.J., USA) for 1 hour at room temperature.

Preparation of Bacterial Cultures

Methicillin sensitive (MSSA, catalog number 29213) and methicillin resistant (MRSA, catalog number 33591) strains of *S. aureus* were obtained from the American Type Culture Collection (Manassas, Va., USA) and grown aerobically in tryptic soy broth or nutrient broth (both from BD), respectively, on a shaking incubator at 250 rpm and 37° C. to an OD600 of 0.500 to 0.550 (~1–2×10$^8$ CFU/mL). Cultures were centrifuged at 5000 g for 5 minutes at room temperature. The supernatant was removed and the bacterial pellets were suspended in one-half the original culture volume of PBG. Tubes containing the functionalized or non-functionalized nanoparticles were removed from the orbital shaker and 0.5 mL of the bacterial suspension was added to each tube. For non-treated control samples, 0.5 mL of the bacterial suspension in PBG was added to a tube containing 0.5 mL of PBG without any nanoparticles. All tubes were then returned to the orbital shaker for 90 minutes of incubation at room temperature.

Laser-Induced Photothermal Killing of Bacteria

Laser exposures were performed using an Nd:YAG Q-switched laser (model CRF400, Big Sky/Quantel, Bozeman, Mont., USA) with a wavelength of 532 nm, an 8 nanosecond pulse duration, and a pulse repetition rate of 1 Hz. The optical system included a 250-mm focal length lens and a variable aperture arranged to provide a 2-mm diameter beam with a maximum energy density of approximately 5 J/cm$^2$/pulse. In some experiments, neutral density filters were placed in the beam path to reduce the pulse energy. A Nova II Laser Energy Meter with a Pyroelectric Energy Sensor (model PE25BF-DIF-C) and StarLab 2.0 software (all from Newport, Irvine, Calif., USA) were used to measure and record the pulse energies for each experiment. Laser dosimetry was performed immediately pre- and post-exposure by recording the energy of 10 successive pulses. These pre- and post-exposure values were combined to calculate the mean exposure energy, which was used to calculate laser fluence (energy per unit area) assuming a 2-mm beam diameter.

Triplicate or quadruplicate 75-uL aliquots from each bacterial sample were exposed in quartz cuvettes with a 2 mm wide window and 10 mm light path (Precision Cells, Farmingdale, N.Y., USA). For sham exposures, samples were transferred to cuvettes and placed in the exposure set up for the approximate duration of laser treatment but the laser was not activated. After irradiation with 100 pulses or sham exposure, the aliquots were transferred to fresh tubes, serially diluted in PBS, and plated in triplicate on tryptic soy agar. Bacterial colonies were counted after overnight incubation at 37° C. Statistical analysis of results was conducted using STATISTICA software (v. 9.1, StatSoft, Inc, Tulsa, Okla., USA).

Results

FIG. 1 shows targeted killing of methicillin sensitive *S. aureus* (MSSA) with antibody functionalized gold nanoparticles combined with 532 nm laser irradiation (100 pulses, 5 J/cm2). Bacterial survival was determined by colony forming unit assay. The control group, which did not receive GNPs or laser treatment, was set to 100% survival. Values are expressed as Mean+SD. $p=0.0002$ compared to the other three experimental groups was determined by one-way ANOVA followed by post-hoc Tukey HSD test. The results shows antibody functionalized gold nanoparticles combined with 532 nm laser irradiation is effective in significantly reducing bacterial survival.

FIG. 2 is the scanning electron microscope images of a) MSSA, b) MSSA+GNPs without antibody, c) MSSA+GNPs with antibody at 25,000×, and d) MSSA+GNPs with antibody at 100,000× magnification. Images illustrate antibody targeting of GNPs to MSSA. Bottom four panels show MSSA treated with antibody-conjugated GNPs and exposed to e) sham treatment (−Laser) or f) through h) pulsed laser irradiation at 532 nm (+Laser). Panels f) through h) show evidence of flattened, dead bacterial cells.

FIG. 3 shows antibacterial effect of antibody targeted gold nanoparticles and pulsed 532 nm laser irradiation against MSSA as a function of laser fluence. MSSA samples were incubated with 40-nm gold nanospheres coated with anti-*S. aureus* antibodies then exposed to 100 laser pulses. Bacterial survival was determined by colony forming unit assays. The control group which did not receive gold nanoparticles or laser treatment was set to 100% survival. Values are expressed as Mean+SD of six independent experiments.

FIG. 4 shows Antibacterial effect of targeted GNPs and pulsed 532 nm laser irradiation against A) MSSA and B) MRSA. Bacterial samples were incubated with 40-nm gold nanospheres coated with anti-*S. aureus* antibodies then exposed to 100 laser pulses. Bacterial survival was determined by colony forming unit assays. The control group which did not receive gold nanoparticles or laser treatment was set to 100% survival. The antibody functionalized gold nanoparticles combined with 532 nm laser irradiation is shown to be effective in killing drug-resistant *S. aureus*.

Prophetic Example 2

Laser-Induced Opto-Acoustic Killing Of *S. Aureus* Planktonic Cultures

Chitosan is a naturally occurring biopolymer with good biocompatibility and antimicrobial activity against a wide range of bacteria. The ability of chitosan to enhance the antibacterial effect of laser-induced opto-acoustics against methicillin-sensitive and methicillin-resistant S. aureus in planktonic cultures will be tested. First, the anti-bacterial effect of two low molecular weight, and one medium molecular weight chitosan preparations without laser or nanoparticle treatment will be determined by monitoring OD600 over 24 hours in a microtiter plate growth assay. The chitosan preparation with the greatest antibacterial effect in the plate assay will then be tested to determine if it can augment the laser-induced opto-acoustic killing of S. aureus. Testing will include experiments to characterize the chitosan concentrations and incubation times for maximal antimicrobial effect.

Prophetic Example 3

Laser-Induced Opto-Acoustic Treatment To Destroy S. Aureus Biofilms

Develop An In Vitro S. Aureus Biofilm Model

An in vitro biofilm model will be developed using methicillin-sensitive and methicillin-resistant strains of S. aureus, according to published procedures (8, 9). In brief, aliquots of fresh bacterial cultures in broth will be inoculated into wells of 96-well microplates with quartz bottoms and incubated for 24 to 48 hours as needed for formation of biofilms. Light microscopy and crystal violet staining will be used to monitor biofilm formation.

Gold nanospheres coated with streptavidin will be functionalized as described using biotinylated monoclonal antibodies directed against peptidoglycan, protein A, or lipoprotein of S. aureus (10, 11). Methicillin-sensitive and methicillin-resistant S. aureus biofilms will be grown in 96-well microplates as described. Broth will be removed from the wells and the plates and washed with PBS. Aliquots of the functionalized nanospheres will then be added to the microplate wells containing biofilms and the plates will be incubated for 90 minutes at 37° C. The nanoparticle solution will be removed, the wells washed with PBS, and fresh PBS added to the wells. The plates will be placed in a custom-designed 96-well plate holder attached to a computer-controlled gantry XY robotic system and exposed through the top of the well to 8-ns pulsed laser irradiation at 532 nm. Sham exposed samples will be placed within the sample holder but the laser will not be activated. Total biofilm mass will be measured using the crystal violet staining method (9), and selected biofilm samples will be analyzed for bacterial viability using a LIVE/DEAD Biofilm Viability Kit (Invitrogen). Efficacy of the three different types of monoclonal antibodies in targeting the nanoparticles to induce killing of the biofilms will be compared.

Use of adjuvants that are known to weaken the bacterial cell wall and extracellular matrix of biofilms will potentially make the cells more susceptible to the opto-acoustic effects and lower the pulse energy required for maximal antibacterial effect. At this time, possible candidates selected for testing as adjuvants include the endopeptidase lysostaphin, which enzymatically attacks the bacterial cell wall and dispersin B, an enzyme that breaks down the extracellular matrix of staphylococcal biofilms (12). Other possible candidates include antibacterial peptides that weaken the cell wall or membrane such ranalexin and LL-37 (13, 14).

REFERENCES

1. Petersen K, Riddle M S, Danko J R, Blazes D L, Hayden R, Tasker S A, Dunne J R. Trauma-related infections in battlefield casualties from Iraq. Ann Surg. 2007; 245(5): 803-811.
2. Peterson K, Hayes D K, Blice J P, Hale R G. Prevention and management of infections associated with combat-related head and neck injuries. J Trauma. 2008; 64(3): S265-S276.
3. Boucher H W, Corey G R. Epidemiology of methicillin-resistant Staphylococcus aureus. Clin Infect Dis. 2008; 46 Suppl 5:S344-349.
4. Sakoulas G, Moellering R C, Jr. Increasing antibiotic resistance among methicillin-resistant Staphylococcus aureus strains. Clin Infect Dis. 2008; 46 Suppl 5:S360-367.
5. Zharov V P, Mercer K E, Galitovskaya E N, Smeltzer M S. Photothermal nanotherapeutics and nanodiagnostics for selective killing of bacteria targeted with gold nanoparticles. Biophys J. 2006; 90(2):619-627.
6. Embleton M L, Nair S P, Cookson B D, Wilson M. Selective lethal photosensitization of methicillin-resistant Staphylococcus aureus using an IgG-tin (IV) chlorin e6 conjugate. J Antimicrob Chemother. 2002; 50(6):857-64.
7. Galanzha E I, Shashkov E, Sarimollaoglu M, et al. In vivo magnetic enrichment, photoacoustic diagnosis, and photothermal purging of infected blood using multifunctional gold and magnetic nanoparticles. PLoS One. 2012; 7(9): e45557.
8. Sanchez C J Jr, Mende K, Beckius M L, Akers K S, Romano D R, Wenke J C, Murray C K. Biofilm formation by clinical isolates and the implications in chronic infections. BMC Infect Dis. 2013; 13:47.
9. Chen P, Abercrombie J J, Jeffrey N R, Leung K P. An improved medium for growing Staphylococcus aureus biofilm. J Microbiol Methods. 2012; 90(2):115-8.
10. Galanzha E I, Shashkov E, Sarimollaoglu M, Beenken K E, Basnakian A G, Shirtliff M E, Kim J W, Smeltzer M S, Zharov V P. In vivo magnetic enrichment, photoacoustic diagnosis, and photothermal purging of infected blood using multifunctional gold and magnetic nanoparticles. PLoS One. 2012; 7(9):e45557.
11. Brady R A, Leid J G, Kofonow J, Costerton J W, Shirtliff M E. Immunoglobulins to surface-associated biofilm immunogens provide a novel means of visualization of methicillin-resistant Staphylococcus aureus biofilms. Appl Environ Microbiol. 2007; 73(20):6612-9.
12. Kiedrowski M R, Horswill A R. New approaches for treating staphylococcal biofilm infections. Ann N Y Acad Sci. 2011; 1241:104-21.
13. Graham S, Coote P J. Potent, synergistic inhibition of Staphylococcus aureus upon exposure to a combination of the endopeptidase lysostaphin and the cationic peptide ranalexin. J Antimicrob Chemother. 2007 April; 59(4): 759-62.
14. Vandamme D, Landuyt B, Luyten W, Schoofs L. A comprehensive summary of LL-37, the factotum human cathelicidin peptide. Cell Immunol. 2012 November; 280 (1):22-35.

What is claimed is:
1. A nanoparticle, consisting of:
 a. a nanoparticle core, wherein the nanoparticle core is capable of absorbing laser irradiation; and b. a streptavidin-biotin coating disposed on the surface of said nanoparticle core, wherein the coating is capable of binding to a target bacteria including a methicillin resistant bacteria.

2. The nanoparticle core according to claim 1, wherein the nanoparticle core is a metal nanoparticle, a nanoparticle with a core-shell structure, or an electroceramic nanocomposite.

3. The nanoparticle according to claim 1, wherein the nanoparticle core is a gold nanoparticle or a silica nanoparticle coated with a gold shell.

4. The nanoparticle according to claim 1, wherein the streptavidin-biotin coating is capable of binding to Gram-positive bacteria or Gram-negative bacteria.

5. The nanoparticle according to claim 1, wherein the streptavidin-biotin coating is capable of binding to bacteria with surface peptidoglycan.

6. A pharmaceutical composition for treating microbial infection, comprising the nanoparticle according to claim 1, and a pharmaceutically acceptable carrier thereof.

* * * * *